United States Patent [19]

Usami et al.

[11] Patent Number: 5,265,458
[45] Date of Patent: Nov. 30, 1993

[54] METHOD OF COMPENSATING OUTPUT OF AIR/FUEL RATIO SENSOR FOR VARIATION IN THE CURRENT SENSITIVITY TO OXYGEN

[75] Inventors: Jun Usami, Aichi; Motohiro Nishiwaki, Nagoya, both of Japan

[73] Assignee: NGK Insulators, Ltd., Japan

[21] Appl. No.: 896,992

[22] Filed: Jun. 11, 1992

[30] Foreign Application Priority Data

Jun. 14, 1991 [JP] Japan ............... 3-170747

[51] Int. Cl.$^5$ ............................. G01N 30/02
[52] U.S. Cl. ..................... 73/23.32; 204/406
[58] Field of Search ........... 73/16, 23.32, 1 G; 204/406

[56] References Cited

U.S. PATENT DOCUMENTS

| | | | |
|---|---|---|---|
| 4,790,924 | 12/1988 | Logothetis et al. | 204/412 |
| 4,796,587 | 1/1989 | Nakajima et al. | 73/23.32 |
| 4,860,712 | 8/1989 | Nakajima et al. | |
| 4,875,981 | 10/1989 | Usami et al. | |
| 5,034,112 | 7/1991 | Murase et al. | 204/406 |

FOREIGN PATENT DOCUMENTS 62-104152 7/1987 Japan .
62-257056 11/1987 Japan .
62-274255 11/1987 Japan .
2181253 4/1987 United Kingdom .

Primary Examiner—Robert Raevis
Attorney, Agent, or Firm—Parkhurst, Wendel & Rossi

[57] ABSTRACT

Method of compensating an output signal (YA) of a sensor exposed to an exhaust gas produced from an air-fuel mixture, the sensor including an electrochemical sensing cell which produces an electromotive force (Vs) corresponding an oxygen partial pressure in an internal space into which the exhaust gas diffuses with a predetermined resistance, and an oxygen pumping cell to which a pump current (Ip) is applied so as to control the oxygen partial pressure in the internal space such that the electromotive force is held at a constant value. The output signal corresponds to the pump current. The method includes the steps of: converting the analog output signal (YA) into a digital signal (YD) by an analog/digital converter; compensating the analog signal to a first sensitivity compensation, by adjusting an input signal range (FSR) of the analog/digital converter according to a coefficient (KA) which corresponds to a coefficient (KO$_2$) of sensitivity of the pump current of the sensor to the O$_2$ concentration of the exhaust gas.

12 Claims, 4 Drawing Sheets

METHOD OF COMPENSATING OUTPUT OF AIR/FUEL RATIO SENSOR FOR VARIATION IN THE CURRENT SENSITIVITY TO OXYGEN

BACKGROUND OF THE INVENTION

1. Field of the Invention

The present invention relates generally to a method of compensating the output of an exhaust gas sensor or air/fuel ratio sensor, and more particularly to a method of compensating the output of such an air/fuel ratio sensor, for improved accuracy of measurement or determination, or regulation or control of the air/fuel ratio of an air-fuel mixture supplied to an internal combustion engine of a motor vehicle or an industrial furnace.

2. Discussion of the Prior Art

In the art of measuring the air/fuel ratio (A/F ratio) or other parameter of an air/fuel mixture used for an automotive internal combustion engine or an industrial furnace, there is known an exhaust gas sensor or air/fuel ratio sensor of a so-called double-cell type which uses in combination an electrochemical cell in the form of an oxygen concentration cell, and another electrochemical cell in the form of an oxygen pumping cell. In use, the air/fuel ratio sensor is exposed to an exhaust gas produced as a result of combustion of the air-fuel mixture. Since the level of output signal of the air/fuel ratio sensor has known relationships with the contents of the individual components of the exhaust gas, a parameter or parameters of the air-fuel mixture such as the air/fuel ratio (A/F), excess oxygen ratio ($\lambda$) and oxygen concentration ($+O_2$ or $-O_2$) can be determined based on the output signal of the sensor.

Each of the two electrochemical cells of the double-cell type air/fuel ratio sensor uses an oxygen-ion conductive solid electrolyte body, and at least one pair of electrodes provided on the solid electrolyte body. Between the two electrochemical cells, there is formed an internal space into which the exhaust gas under measurement is introduced under a predetermined diffusion resistance. The first or oxygen concentration sensing cell (hereinafter referred to as "sensing cell") produces an electromotive force depending upon the partial pressure of oxygen in the internal space, according to the Nernst equation, while the second or oxygen pumping cell (hereinafter referred to as "pumping cell") operates to perform an oxygen pumping action so as to regulate the oxygen partial pressure within the internal space of the sensor so that the electromotive force induced by the sensing cell is held at a predetermined constant level which corresponds to the stoichiometric point (A/F=14.6; $\lambda=1$). The pump current applied to the pumping cell is used as the output of the air/fuel ratio sensor, which reflects the composition of the exhaust gas.

More specifically described, the pump current Ip applied to the pumping cell in this double-cell type of air/fuel ratio sensor is obtained according to the following equation (1):

$$Ip = KO_2 \cdot PO_2 - KCO \cdot PCO - KH_2 \cdot PH_2 \qquad (1)$$

where,
$KO_2$: $O_2$ concentration current sensitivity coefficient
$PO_2$: Partial pressure of $O_2$ in exhaust gas
$KCO$: CO concentration current sensitivity coefficient
$PCO$: Partial pressure of CO in exhaust gas
$KH_2$: $H_2$ concentration current sensitivity coefficient
$PH_2$: Partial pressure of $H_2$ in exhaust gas The output of the sensor in the form of the pump current Ip is then processed to calculate the A/F ratio, etc., according to the following formulas (2A) and (2B) and equation (3). The formulas (2A) and (2B) are associated with the numbers of the individual components of the air-fuel mixture before combustion and those of the exhaust gas produced as a result of combustion of the air-fuel mixture.

i) Air-Fuel Mixture Before Combustion:

$$CmHn + \lambda \cdot \{O_2 + (m+n/4) \cdot (79.05/20.95) \cdot N_2\} \qquad (2A)$$

ii) Exhaust Gas Produced by Combustion of Air-Fuel Mixture:

$$A_1 \cdot CO + A_2 \cdot CO_2 + A_3 \cdot H_2 + A_4 \cdot H_2O + A_5 \cdot O_2 + A_6 \cdot N_2 \qquad (2B)$$

where,
CmHn: Carbon-hydrogen fuel
m: Number of carbon component in 1 mole of the fuel
n: Number of hydrogen component in 1 mole of the fuel
$\lambda$: Excess air ratio
$A_1$–$A_6$: Numbers of the appropriate components in exhaust gas Generally, $A_1 \cdot CO$ and $A_3 \cdot H_2$ are approximately 0% where $\lambda \geq 1$, and are not 0% where $\lambda < 1$.

$$K(t) = (PCO \cdot PH_2)/(PCO_2 \cdot PH_2) \qquad (3)$$

where,
PCO: Partial pressure of CO in exhaust gas
$PH_2O$: Partial pressure of $H_2O$ in exhaust gas
$PCO_2$: Partial pressure of $PCO_2$ in exhaust gas
$PH_2$: Partial pressure of $H_2$ in exhaust gas The current sensitivity coefficients $KO_2$, $KCO$ and $KH_2$ in the equation (1) are coefficients of sensitivity of the pump current Ip to the concentrations of the gas components $O_2$, CO and $H_2$ of the exhaust gas. These coefficients $KO_2$, $KCO$ and $KH_2$ are constants which are determined and influenced by specific characteristics of the individual sensors, such as the diffusion resistance under which the exhaust gas is introduced into the internal space of the sensor. In other words, the actual current sensitivity coefficients of one sensor differ from those of another sensor, since the individual sensors more or less have dimensional or other manufacturing errors or deviations from the nominal values.

Therefore, the outputs of the individual sensors should be compensated for the variations in the actual current sensitivity coefficients of the gas components of the exhaust gas, by actually measuring those current sensitivity coefficients when the sensors are exposed to a calibrating gas. Otherwise, the output of one sensor may differ from that of another sensor, even when the exhaust gases to be measured by these sensors have the same composition. Thus, the individual sensors should be calibrated for compensation of their outputs for the difference in the actual current sensitivity coefficients of the individual sensors.

Laid-open Publication No. 62-257056 (published in 1987) of unexamined Japanese Patent Application discloses an example of recently proposed methods for easy and precise compensation of the outputs of the individual sensors for the difference in the actual coefficients of sensitivity of the pump current to the gas components of the exhaust gas. In the method disclosed therein, the analog output signal of the sensor is first converted into a digital signal by an A/D converter, and the digital signal is processed for compensating the sensor output according to the actual current sensitivity coefficients of the sensor.

In the presence of the difference or variation in the actual current sensitivity coefficients of the individual sensors, the range over which the output level of a given sensor changes in operation may considerably differ from that of another sensor. In the above-indicated method, therefore, the range of change in the output level of a sensor may be extremely narrower than the nominal range FSR of the input signal of the A/D converter, which is defined by the maximum and minimum levels of the input analog signal, which is the output of the sensor, usually in the form of a voltage signal. In this case, a quantizing error which occurs upon conversion of the analog signal into a digital signal by the A/D converter will have a considerably large influence on the digital output of the A/D converter, whereby the sensing accuracy of the sensor is deteriorated.

For example, if the maximum pump current (Ipmax) obtained with respect to a given calibrating gas is 10 mA for one sensor, and 2 mA for another sensor, due to different current sensitivity coefficients of the two sensors, the maximum level of the analog voltage signal applied to the A/D converter for the former sensor is five times as high as that of the analog voltage signal applied to the A/D converter for the latter sensor. In this case, the amount of error included in the obtained digital output signal of the A/D converter for the latter sensor due to the quantizing error is five times as large as that for the former sensor.

No solutions have been heretofore proposed to effectively deal with the deterioration of the sensing accuracy of the known air/fuel ratio sensors due to the quantizing error described above. The only method to avoid this accuracy deterioration has been to measure or detect the actual output characteristics of the individual sensors and use only the sensors whose output characteristics meet the predetermined standards.

An A/D converter has generally an electrical tendency that the quantizing error becomes excessively large when the level of the analog input signal is less than 1/5 of the nominal input signal range FSR of the converter. Where the sensor is used as an air/fuel ratio sensor exposed to an exhaust gas of an automotive engine, the sensing accuracy tends to be comparatively low because the level of the input analog signal of the A/D converter is relatively low, since the air/fuel ratio of an air-fuel mixture which produces the exhaust gas is controlled to be close to the stoichiometric point (14.6), which means that the input level of the A/D converter and the output level of the air/fuel ratio sensor are usually zero or close to zero. Consequently, the sensor suffers from low sensing accuracy due to a large influence of the quantizing error of the A/D converter.

SUMMARY OF THE INVENTION

The present invention was developed in the light of the drawback experienced in the prior art as described above. It is therefore an object of the present invention to provide a method of compensating the output of an air/fuel ratio sensor, for improved accuracy of measurement or determination of the air/fuel ratio or other parameter or parameters of an air-fuel mixture, by minimizing or eliminating the sensing error experienced in the prior art.

The above object may be achieved according to one aspect of this invention, which provides a method of compensating an output signal (YA) of an air/fuel ratio sensor exposed to an exhaust gas produced as a result of combustion of an air-fuel mixture, the sensor having an internal space into which the exhaust gas is introduced under a predetermined diffusion resistance, and including a first and a second electrochemical cell each of which has an oxygen-ion conductive solid electrolyte body and at least one pair of electrodes, the first electrochemical cell operating as an oxygen concentration cell so as to produce an electromotive force (Vs) which corresponds to an oxygen partial pressure in the internal space, the second electrochemical cell performing an oxygen pumping action with a pump current (Ip) applied thereto so as to control the oxygen partial pressure in the internal space such that the electromotive force is substantially held at a predetermined constant value, the output signal corresponding to the pump current and representing a parameter of the air-fuel mixture, the method comprising the steps of: (a) converting the output signal in the form of an analog signal (YA) into a digital signal (YD) by an analog/digital converter; subjecting the analog signal to a first sensitivity compensation to thereby compensate the digital signal, by adjusting an input signal range (FSR) of the analog/digital converter according to a first sensitivity compensating coefficient (KA) which corresponds to a coefficient ($KO_2$) of sensitivity of the pump current (Ip) of the sensor to an $O_2$ concentration of the exhaust gas.

In the output compensating method of the present invention as described above, the input signal range (FSR) of the A/D converter is adjusted depending upon the first sensitivity compensating coefficient (KA) which corresponds to the coefficient ($KO_2$) of sensitivity of the pump current (Ip) of the pumping cell of the sensor to the oxygen concentration of the exhaust gas. Namely, the input signal range (FSR) of the A/D converter is set according to the coefficient of sensitivity of the pump current of the specific sensor to the oxygen concentration of the exhaust gas. Consequently, the error included in the output signal of the sensor due to the deviation of the $O_2$ sensitivity coefficient of the sensor from the nominal value can be effectively eliminated or minimized by the first sensitivity compensation using the first sensitivity compensating coefficient. Further, the present arrangement reduces the influence of the quantizing error of the A/D converter on the digital signal, which may be eventually processed to provide an output signal of a sensing system. The sensing system includes the sensor, the means for compensating the output signal of the sensor, and means for processing the compensated digital signal. The present output compensating method assures improved sensing stability and accuracy of the sensing system.

In one preferred form of the present invention, the method further comprises the steps of subjecting the digital signal compensated by the first sensitivity compensating coefficient (KA), to a bias compensation by an amount (Y0) equal to a difference between an actual output and a theoretical output of the sensor when the sensor air-fuel mixture has a stoichiometric air/fuel ratio. This bias compensation is useful, since the output level of the sensor when the air-fuel mixture has the stoichiometric air/fuel ratio may usually deviate from the theoretical value.

In another preferred form of this invention, the method further comprises the step of subjecting the digital signal (YD) to a second sensitivity compensation by a second sensitivity compensating coefficient (KM) which corresponds to coefficients (KH$_2$, KCO$_2$) of sensitivity of the pump current of the sensor to H$_2$ and CO$_2$ concentrations of the exhaust gas, if the digital signal indicates that an air/fuel ratio of the air-fuel mixture is smaller than a stoichiometric point. This second sensitivity compensation depending upon the sensitivity coefficients (KH$_2$, KCO$_2$) assures sufficiently high degrees of the sensing stability and accuracy, even when the sensor is used as a rich-burn sensor for controlling the air/fuel ratio of the air-fuel mixture so that the mixture is held to be a fuel-rich mixture.

In the above form of the invention, the step of subjecting the digital signal (YD) to a second sensitivity compensation may comprise: introducing into the internal space of the sensor a calibrating gas whose H$_2$ and CO$_2$ concentrations are known; detecting an actual level of the digital signal (YD) while the sensor is exposed to the calibrating gas; and determining the second sensitivity compensating coefficient (KM) based on a ratio of the actual level to a theoretical level which is calculated based on the H$_2$ and CO$_2$ concentrations of the calibrating gas. The digital signal (YD) may be subjected to the second sensitivity compensation after the digital signal is subjected to the bias compensation.

In a further preferred arrangement of the invention, the method further comprises the steps of detecting a level of the output signal, and amplifying the output signal with an amplification factor which is determined by the detected level of the output signal. In this case, the step of detecting a level of the output signal may comprise determining whether or not the level of the output signal is smaller than a predetermined lower limit, and the step of amplifying the output signal may comprise amplifying the output signal with a first amplification factor of 1 if the level of the output signal is not smaller than the predetermined lower limit, and amplifying the output signal with a second amplification factor larger than 1 if the level of the output signal is smaller than the predetermined lower limit. The predetermined lower limit may be 1/N of a nominal level of the output signal, and the second amplification factor is equal to N. The present arrangement assures high sensing accuracy even when the level of the output signal is relatively small, namely, even when the air/fuel ratio of the air-fuel mixture is close to the stoichiometric point. This arrangement is significant since the air/fuel ratio is usually controlled to be close to the stoichiometric point.

BRIEF DESCRIPTION OF THE DRAWINGS

The above and optional objects, features and advantages of this invention will be better understood by reading the following detailed description of presently preferred embodiments of the invention, when considered in connection with the accompanying drawings, in which.

DETAILED DESCRIPTION OF THE PREFERRED EMBODIMENTS

Figure 1:
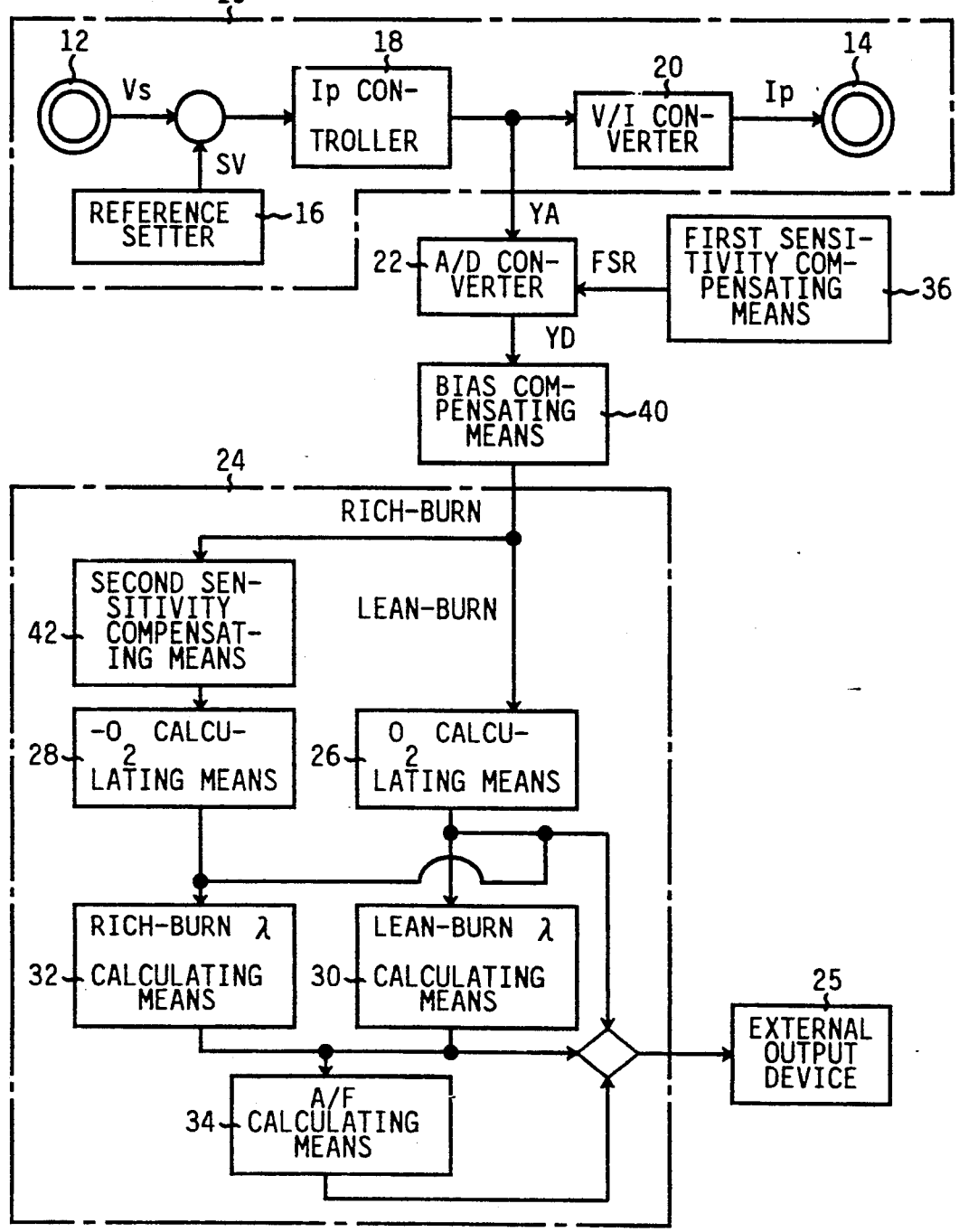
FIG. 1 is a schematic block diagram showing a sensing system, and a method of compensating an output of an air/fuel ratio sensor of the sensing system, according to one embodiment of the present invention.

Referring first to the schematic block diagram of FIG. 1, reference numeral 10 denotes an air/fuel ratio sensor in the form of an oxygen sensor, which is provided as a part of a sensing system. The oxygen sensor 10 is a so-called double-cell type adapted to detect an oxygen concentration of an exhaust gas produced by an internal combustion engine as a result of combustion of an air-fuel mixture. The output of the air/fuel ratio sensor, which represents an air/fuel ratio and other parameters of the air-fuel mixture as described below, is compensated for improved sensing accuracy, according to one embodiment of the present invention.

The air/fuel ratio sensor 10 of the double-cell type has a sensing cell 12 and a pumping cell 14, as known in the art. The sensing cell 12 produces an electromotive force Vs depending upon the oxygen concentration of an atmosphere which is introduced into an internal space in the sensor, under a predetermined diffusion resistance, while the pumping cell 14 operates to perform an oxygen pumping action for pumping oxygen into and out of the internal space. The sensor 10 incorporates an Ip controller 18 which controls a pump current Ip to be supplied to the pumping cell 14, such that the electromotive force Vs induced by the sensing cell 12 is equal to a predetermined reference value SV. As the pump current Ip is thus controlled in a feedback fashion by the Ip controller 18, an analog signal YA which corresponds to the pump current Ip is generated from the Ip controller 18 as the output signal of the air/fuel ratio sensor 10.

In the present air/fuel ratio sensor 10, the analog output signal YA is a voltage signal, which is applied to a voltage/current converter (V/I converter) 20, so that the voltage signal YA is converted into the pump current Ip to be applied to the pump cell 14.

The Ip controller 18 is also connected to an analog/digital converter (A/D converter) 22, so that the analog output signal YA of the sensor 10, which varies with the oxygen concentration of the exhaust gas, is converted into a digital signal YD by the A/D converter 22. The digital signal YD is fed to a signal processing device 24 of the sensing system. The signal processing device 24 processes the received digital input signal YD to provide output signals representative of the oxygen concentrations $\pm O_2$, air/fuel ratio A/F, excess oxygen ratio of the air-fuel mixture, according to known relationships between the level of the output signal YA (YD) of the sensor 10 and the appropriate parameters $\pm O_2$, $\lambda$ and A/F of the air-fuel mixture. The output signals of the signal processing device 24 are fed to an external output device 25 which includes a display for indicating the calculated parameters.

Generally, the signal processing device 24 operates to first calculate the oxygen concentrations $\pm O_2$ based on the digital signal YD from the A/D converter 22, according to the equations and formulas (1), (2A), (2B) and (3) indicated above. When the value of the digital output signal YD is zero or positive (YD≧0), namely, when the air-fuel mixture is a fuel-lean mixture (lean-burn mixture) having an air/fuel ratio equal to or larger than the stoichiometric point, the digital signal YD is processed by $O_2$ calculating means 26 for calculating the oxygen concentration ($O_2$), according to the following equation (4):

$$YD/KO_2 = PO_2 \qquad (4)$$

where,
YD: Output of air/fuel ratio sensor
$KO_2$: $O_2$ concentration current sensitivity coefficient
$PO_2$: Partial pressure of $O_2$ in exhaust gas When the value of the digital output signal YD is negative (YD<0), namely, when the air-fuel mixture is a fuel-rich mixture (rich-burn mixture) having an air/fuel ratio smaller than the stoichiometric point, on the other hand, the digital signal YD is applied to $-O_2$ calculating means 28 for calculating the oxygen concentration $-O_2$, according to the following equations (5A) and (5B):

$$YD = KO_2(KCO \cdot PCO + KH_2 \cdot PH_2) \qquad (5A)$$

$$PO_2 = -(PCO + PH_2)/2 \qquad (5B)$$

where,
YD: Output of air/fuel ratio sensor
$KO_2$: $O_2$ concentration current sensitivity coefficient
KCO: CO concentration current sensitivity coefficient
PCO: Partial pressure of CO in exhaust gas
$KH_2$: $H_2$ concentration current sensitivity coefficient
$PH_2$: Partial pressure of $O_2$ in exhaust gas
$PO_2$: Partial pressure of $O_2$ in exhaust gas It will be understood from the equations (4) and (5A) and (5B) that the calculation of the oxygen concentration ($O_2$) where YD≧0 is relatively simple, while the calculation of the oxygen concentration $-O_2$ where YD<0 is considerably complicated. For calculating the oxygen concentration $-O_2$, therefore, it is preferable to use an inverse linearizing function $F^{-1}(\ )$ as obtained according to the following equation (6), from a linearizing function $F(\ )$ in the form of an approximating curve or a multi-dimensional polynominal function, which represents a relationship between the level of the digital signal YD and the partial oxygen pressure $P(-O_2)$, that corresponds to the hydrogen/carbon ratio of the air-fuel mixture:

$$YD/KO_2 = KCO \cdot PCO + KH_2 \cdot PH_2 = F(P(-O^2)) \qquad (6)$$

therefore, $F^{-1}(YD/KO_2) = P(-O_2)$ where,
YD: Output of air/fuel ratio sensor
$KO_2$: $O_2$ concentration current sensitivity coefficient
KCO: CO concentration current sensitivity coefficient
PCO: Partial pressure of CO in exhaust gas
$KH_2$: $H_2$ concentration current sensitivity coefficient
$PH_2$: Partial pressure of $H_2$ in exhaust gas
$P(-O_2)$: Partial pressure of $-O_2$ in exhaust gas
$F(\ )$: Linearizing function
$F^{-1}(\ )$: Inverse linearizing function For calculating the excess oxygen ratio λ of the air-fuel mixture, the outputs of the calculating means 26, 28 representing the oxygen concentration values $O_2$ and $-O_2$ are processed by lean-burn λ calculating means 30 and rich-burn λ calculating means 32, respectively. Further, the outputs of the lean-burn and rich-burn λ calculating means 30, 32 are used by A/F calculating means 34 to calculate the air-fuel ratio A/F of the air-fuel mixture. These calculations are effected according to known equations, and the calculated parameters $O_2$, $-O_2$, λ and A/F are selectively or concurrently indicated on the display of the external output device 25.

In the present sensing system, first sensitivity compensating means 36 is connected to the A/D converter 22, so that the output signal YA of the sensor 10 applied to the A/D converter 22 is compensated by the first sensitivity compensating means 36, whereby the digital signal YD fed to the signal processing device 24 is accordingly compensated. This first sensitivity compensation of the output signal YA of the sensor 10 by the first sensitivity compensating means 36 is effected to minimize the sensing error of the sensor 10, that is, errors of the output signals of the signal processing device 24, which arise from a variation in the coefficient $KO_2$ of sensitivity of the pump current (Ip) of the individual sensors 10 to the $O_2$ concentration of the exhaust gas. The sensitivity coefficient $KO_2$ is used in the equation (4) for calculating the oxygen partial pressure of the exhaust gas. The variation in the coefficient $KO_2$, which arises from manufacturing errors of the sensors, causes a variation in the range in which the levels of the output signals YA of the individual sensors 10 change in operation.

More specifically, the first sensitivity compensation by the first compensating means 36 is achieved by setting the input voltage range FSR of the A/D converter 22, depending upon the O2 concentration current sensitivity coefficient $KO_2$ of each specific sensor 10. First, the output signal levels of the signal processing device 24 are actually detected while the sensor 10 is exposed to the calibrating gas which has a known composition that satisfies YD≧0. Further, the theoretical output signal levels of the signal processing device 24 are calculated based on the known composition of the calibrating gas. The input voltage range FSR of the A/D converter 22 is adjusted so that the actually detected output signal levels of the signal processing device 24 coincide with the calculated theoretical levels.

As a result of the first sensitivity compensation by suitably adjusting the input voltage range FSR of the A/D converter 22, the analog output signal YA is amplified by 1/K as indicated by the following equation (7), before conversion of the signal YA into the digital signal YD, where the range FSR is 1/KA of a nominal or reference value for the sensor which exhibits the desired or nominal output characteristics. The value KA is referred to as a first sensitivity compensating coefficient.

$$YD = YA/KA \qquad (7)$$

Thus, the output signal YD applied to the signal processing device 24 is compensated so that the actually detected output levels of the signal processing device 24 coincide with the theoretical or nominal levels, where YD≧0.

The first sensitivity compensating coefficient KA used for the first sensitivity compensation by the first sensitivity compensating means 36 corresponds to the variation in the current sensitivity coefficient $KO_2$ of the individual sensors 10 associated with the $O_2$ concentration of the exhaust gas. The coefficient KA functions to eliminate the variation in the output levels of the individual sensors 10 due to the variation in the coefficient $KO_2$, where $YD \geq 0$.

It will be understood that the input voltage range FSR of the A/D converter 22 is adjusted by the first sensitivity compensating means 36, depending upon the $O_2$ concentration current sensitivity coefficient $KO_2$ of the specific sensor 10, namely, depending upon the the maximum and minimum levels of the output signal YA of the sensor 10. Therefore, even if the level of the output signal YA of the specific sensor 10 is lower than the nominal value, the quantizing error upon conversion by the A/D converter 22 of the analog input signal YA into the digital output signal YD will have an effectively minimized influence on the output signals ($\pm O_2$, $\lambda$ and A/F) of the signal processing device 24.

Assuming that the levels of the output signals YA of two sensors 10 named sensors $\alpha$ and $\beta$ are 10 V and 2 V, respectively, for example, when these sensors $\alpha$ and $\beta$ are exposed to the same calibrating gas (having the known composition for $YD \geq 0$), the input voltage range FSR of the A/D converter 22 of the sensor $\beta$ is set to be 1/5 of that of the sensor $\alpha$, with the first sensitivity compensating coefficient KA for the sensor $\beta$ being set to "5" (KA=5). As a result of this first sensitivity compensation by the compensating means 36, the levels of the digital signals YD obtained from the A/D converters 22 of the two sensors $\alpha$ and $\beta$ are substantially the same, and the digital signals YD of the two sensors are substantially free from errors due to the difference in the $O_2$ concentration current sensitivity coefficient $KO_2$ of the two sensors $\alpha$ and $\beta$, whereby the output signals of the signal processing devices 24 obtained from these signals YD of the two sensors include substantially the same (and sufficiently small) amounts of errors due to the quantizing error of the A/D converters 22.

Figure 2:
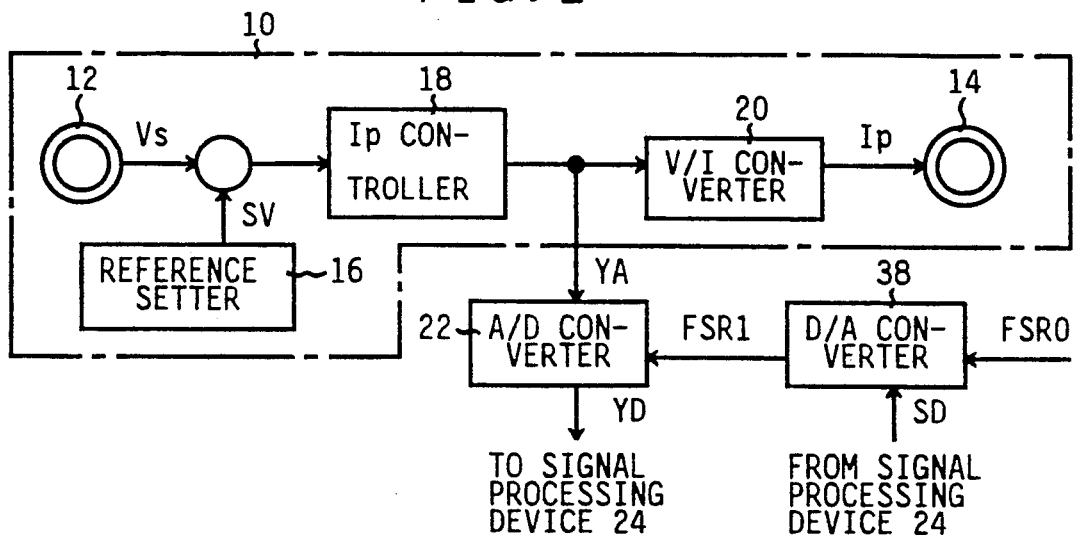
FIG. 2 is a block diagram illustrating one form of the method of FIG. 1 wherein a D/A converter is used as first sensitivity compensating means.

The first sensitivity compensating means 36 may be a digital/analog converter (D/A converter) 38 as illustrated in FIG. 2, where the output signals produced by the calculating system 24 are digital signals as in the arrangement of FIG. 1. In this case, the D/A converter 38 deals with the same number (n) of bits (binary digits) as the A/D converter 22. Suppose a digital output signal SD is obtained from the signal processing device 24, an input range $FSR_0$ of the A/D converter 38 is changed based on the digital signal SD, to change an input voltage range $FSR_1$ of the A/D converter 22, according to the following equation (8):

$$FSR_1 = (SD \cdot FSR_0)/(2^n - 1) \quad (8)$$

where,
$FSR_1$: FSR of A/D converter 22
$FSR_0$: FSR of D/A converter 38
SD: Measured air/fuel ratio
n: Number of bits In this case, the $SD/(2^n - 1)$ is the first sensitivity compensating coefficient KA indicated above.

The digital output signal YD of the A/D converter 22 which has been compensated by the first sensitivity compensating coefficient KA by the first sensitivity compensating means 36 is further compensated by bias compensating means 40 interposed between the A/D converter 22 and the signal processing device 24. That is, the manufacturing errors of the specific sensor 10 cause not only the variation in the $O_2$ concentration current sensitivity coefficient $KO_2$ discussed above, but also a bias error of the digital signal YD, which is a deviation of the level of the signal YD where the excess oxygen ratio $\lambda = 1$, from the theoretical or nominal value. The bias compensating means 40 compensates the signal YD for this bias error.

The level of the output signal of the signal processing device 24 is actually detected when the sensor 10 is exposed to the calibrating gas whose composition corresponds to the stoichiometric point ($\lambda = 1$) of the air-fuel mixture. A bias compensating value Y0 used by the bias compensating means 40 for compensating the digital value YD is determined such that the actually detected output signal level of the signal processing device 24 coincides with the theoretical value. That is, the digital signal YD compensated by the first sensitivity compensating coefficient KA used in the above equation (7) is further compensated by the bias compensating means 40, as indicated by the following equation (9), which further includes the bias compensating value Y0:

$$YD = (YA - Y0)/KA \quad (9)$$

Thus, the bias error otherwise included in the digital signal YD is eliminated or minimized so that the level of the signal YD corresponding to the stoichiometric excess oxygen ratio $\lambda = 1$ coincides with the theoretical level.

The digital signal YD thus subjected to the first sensitivity compensation and the bias error compensation by the compensating means 36, 40 is fed to the signal processing device 24. When the value of the signal YD is zero or positive (when the air-fuel mixture is a lean-burn mixture), the signal YD is processed by the $O_2$ calculating means 26. When the value of the signal YD is negative (when the air-fuel mixture is a rich-burn mixture), the signal YD is processed by the $-O_2$ calculating means 28. The signal processing device 24 incorporates second sensitivity compensating means 42 for effecting second sensitivity compensation of the signal YD, which will be described.

When the air/fuel mixture which produces an exhaust gas to be detected by the sensor 10 is a fuel-rich or rich-burn mixture having an air/fuel ratio smaller than the stoichiometric point (14.6), the output of the sensor is influenced by the coefficients $KH_2$ and $KCO_2$ of sensitivity of the pump current Ip to the concentrations of the $H_2$ and $CO_2$ components. These current sensitivity coefficients $KH_2$ and $KCO_2$ of one sensor differ from those of another sensor, due to the manufacturing errors of the individual sensors. The second sensitivity compensation by the second sensitivity compensating means 42 is effected to minimize the error of the sensor output due to the variation or difference in the current sensitivity coefficients $KH_2$ and $KCO_2$ associated with the $H_2$ and CO2 concentrations of the exhaust gas.

To effect the second sensitivity compensation, the levels of the output signals of the signal processing device 24 are detected when the sensor 10 in question is exposed to the calibrating gas whose $H_2$ and $CO_2$ concentrations are known. A second sensitivity compensating coefficient KM is determined so that the detected output levels coincide with the theoretical or nominal levels corresponding to the calibrating gas. Namely, the second sensitivity compensating coefficient KM is determined based on a ratio of the detected output levels to the theoretical levels which are calculated based on the $H_2$ and $CO_2$ concentrations of the calibrating gas.

The digital signal YD which has been compensated by the first compensating coefficient KA and the bias compensating value Y0 which are included in the above equation (9) is further compensated by the second sensitivity compensating means 42, as indicated by the following equation (10), which further includes the second sensitivity compensating coefficient KM:

$$YD = (YA - Y0)/(KA \cdot KM) \qquad (10)$$

The second sensitivity compensating coefficient KM used for the second sensitivity compensation by the second sensitivity compensating means 42 corresponds to the variations in the current sensitivity coefficients $KH_2$ and $KCO_2$ of the individual sensors 10 associated with the $H_2$ and $CO_2$ concentrations of the exhaust gas. The coefficient KM functions to eliminate the variation in the output levels of the individual sensors 10 due to the variation in the coefficients $KH_2$ and $KCO_2$, where $YD \geq 0$.

According to the second sensitivity compensation described above, the digital output signal YD of the sensor 10 is compensated by the second sensitivity compensating coefficient KM which is obtained based on the actually detected output of the signal processing device 24, so as to eliminate the variations in the current sensitivity coefficients $KH_2$ and $KCO_2$ of the specific sensor 10 from the nominal values. This second sensitivity compensation assures easier and more efficient and accurate compensation of the sensor output for the $KH_2$ and $KCO_2$ variations, than the compensation using a stored data map representative of a compensating graph or pattern.

In the present embodiment of the invention, the output signal YA of the sensor 10 is subjected to the first sensitivity compensation using the first sensitivity compensating coefficient KA, the bias error compensation using the bias compensating value Y0, and the second sensitivity compensating using the second sensitivity compensating coefficient KM. As a result, the oxygen partial pressure $PO_2$ of the exhaust gas produced by a fuel-lean air-fuel mixture, which is otherwise calculated according to the equation (4), is calculated by the $O_2$ calculating means 26 according to the following equation (11), while the oxygen partial pressure $P(-O_2)$ of the exhaust gas produced by a fuel-rich air-fuel mixture, which is otherwise calculated according to the equation (6), is calculated by the $-O_2$ calculating means 32 according to the following equation (12):

$$(YD - Y0)/KA = PO_2 \qquad (11)$$

where,
YD: Output of air/fuel ratio sensor
Y0: Bias compensating value
KA: First sensitivity coefficient
$PO_2$: Partial pressure of $O_2$ in exhaust gas $$F^{-1}((YD - Y0)/(KA \cdot KM)) = P(-O_2) \qquad (12)$$

where,
YD: Output of air/fuel ratio sensor
Y0: Bias compensating value
KA: First sensitivity coefficient
KM: Second sensitivity coefficient
$F^{-1}(\ )$: Inverse linearizing function
$P(-O_2)$: Partial pressure of $-O_2$ in exhaust gas It will be understood that the equation (11) used by the $O_2$ calculating means 26 includes the first sensitivity compensating coefficient KA and the bias compensating value Y0, while the equation (12) used by the $-O_2$ calculating means 32 includes the first and second sensitivity compensating coefficients KA and KM and the bias compensating value Y0.

According to the present method or system of compensating the output of the air/fuel ration sensor, the outputs of the individual sensors 10 are effectively and suitably compensated for the variations in the sensitivity coefficients $KO_2$, $KH_2$ and $KCO_2$ of the sensors 10 associated with the concentrations of $O_2$, $H_2$ and $CO_2$ of the exhaust gas, and for the variation in the bias error, i.e., variation in the output level when the air-fuel mixture has the stoichiometric air/fuel ratio (A/F = 14.6) or oxygen excess ratio ($\lambda = 1$). The first sensitivity compensation using the coefficient KA for adjusting the input voltage range FSR of the A/D converter 22 assures a minimum output error of each sensor 10 due to the quantizing error upon conversion of the analog signal YA into the digital signal YD by the A/D converter 22.

Referring next to the block diagram of FIG. 3, there will be described a second embodiment of this invention, wherein the same reference numerals as used in FIG. 1 are used to identify the functionally corresponding elements, which will not be described to avoid redundant explanation thereof.

The present second embodiment uses a 1/N level detector 46 and a selective amplifier 44, in addition to the elements provided in the first embodiment of FIG. 1. The 1/N level detector 46 functions to determine whether the level of the analog output signal YA of the sensor 10 is smaller than a predetermined lower limit of 1/N of the nominal value, for example, 1/5 of the nominal value (level of the signal YA of the nominal sensor 10). The output signal of the 1/N level detector 46 indicative of this determination is applied to the selective amplifier 44. The selective amplifier 44 amplifies the analog output signal YA by the N-fold amount when the level of the analog signal YA is smaller than 1/N of the nominal value. Namely, an amplification factor G of the selective amplifier 44 is equal to 1 when the detected level of the output signal YA is not smaller than 1/N of the nominal value, and is equal to N when the detected output level is smaller than 1/N of the nominal value.

For example, where the 1/N level detector 46 determines whether the output signal YA of the sensor 10 is smaller than 1/5 of the nominal value, the selective amplifier 44 operates to amplify the signal YA five times, or the amplification factor G of the amplifier 44 is set to 5, when the output signal from the detector 46 indicates that the signal YA is smaller than 1/5 of the nominal value.

The output signal of the 1/N level detector 46 is fed also to the bias compensating means 40 and the $O_2$ and $-O_2$ calculating means 26, 28.

When the output signal from the detector 46 indicates that the output YA is smaller 1/N of the nominal value, the bias compensating means 40 modifies the bias compensating value Y0 to Y0' according to the amplification factor G of the selective amplifier 44, as indicated by the following equations (13A) and (13B):

$$YD = (YA - Y0')/KA \qquad (13A)$$

$$Y0' = Y0 \cdot G \qquad (13B)$$

Since the bias error of the digital output signal YD of the A/D converter 22 increases when the selective amplifier 44 operates with the amplification factor G, the bias compensating value Y0 should be increased according to the amplification factor G, as indicated by the equation (13B).

Further, the level of the digital signal YD (more precisely, YD−Y0') applied to the $O_2$ and $-O_2$ calculating means 26, 28 when the selective amplifier 44 operates with the amplification factor G is divided by the amplification factor G, as indicated by the following equations (14) and (15), in order to eliminate the influence of the amplification of the signal YA by the selective amplifier 44.

$$(YD - Y0')/(KA \cdot G) = PO_2 \quad (14)$$

where,
YD: Output of air/fuel ratio sensor
Y0': Bias compensating value
G: Amplification factor of selective amplifier
KA: First sensitivity coefficient
$PO_2$: Partial pressure of $O_2$ in exhaust gas $$F^{-1}(YD - Y0')/(KA \cdot KM \cdot G) = P(-O_2) \quad (15)$$

where,
YD: Output of air/fuel ratio sensor
Y0': Bias compensating value
G: Amplification factor of selective amplifier
KA: First sensitivity coefficient
KM: Second sensitivity coefficient
$F^{-1}(\ )$: Inverse linearizing function
$P(-O_2)$: Partial pressure of $-O_2$ in exhaust gas In the present second embodiment, the digital output signal YA is amplified by the selective amplifier 44 before it is applied to the A/D converter 22, when the level of the signal YA is smaller than a predetermined lower limit, that is, when the air/fuel ratio of the air-fuel mixture is relatively near the stoichiometric point. Consequently, even if the level of the output signal YA is relatively low, the influence of the quantizing error on the digital output signal YD of the A/D converter 22 is effectively minimized, thereby assuring improved sensing accuracy of the sensor 10.

The use of the 1/N level detector 46 and the selective amplifier 44 is effective for improved sensing stability and accuracy, particularly because the air-fuel mixture supplied to the vehicle engines is generally controlled so that the mixture has an air/fuel ratio equal to or near the stoichiometric point. In other words, the sensor 10 can be suitably used to maintain the air/fuel ratio of the air-fuel mixture at a desired value near the stoichiometric point.

While the present invention has been described in detail in its presently preferred embodiments, for illustrative purpose only, it is to be understood that the invention is not limited to the details of the illustrated embodiments.

Figure 3:
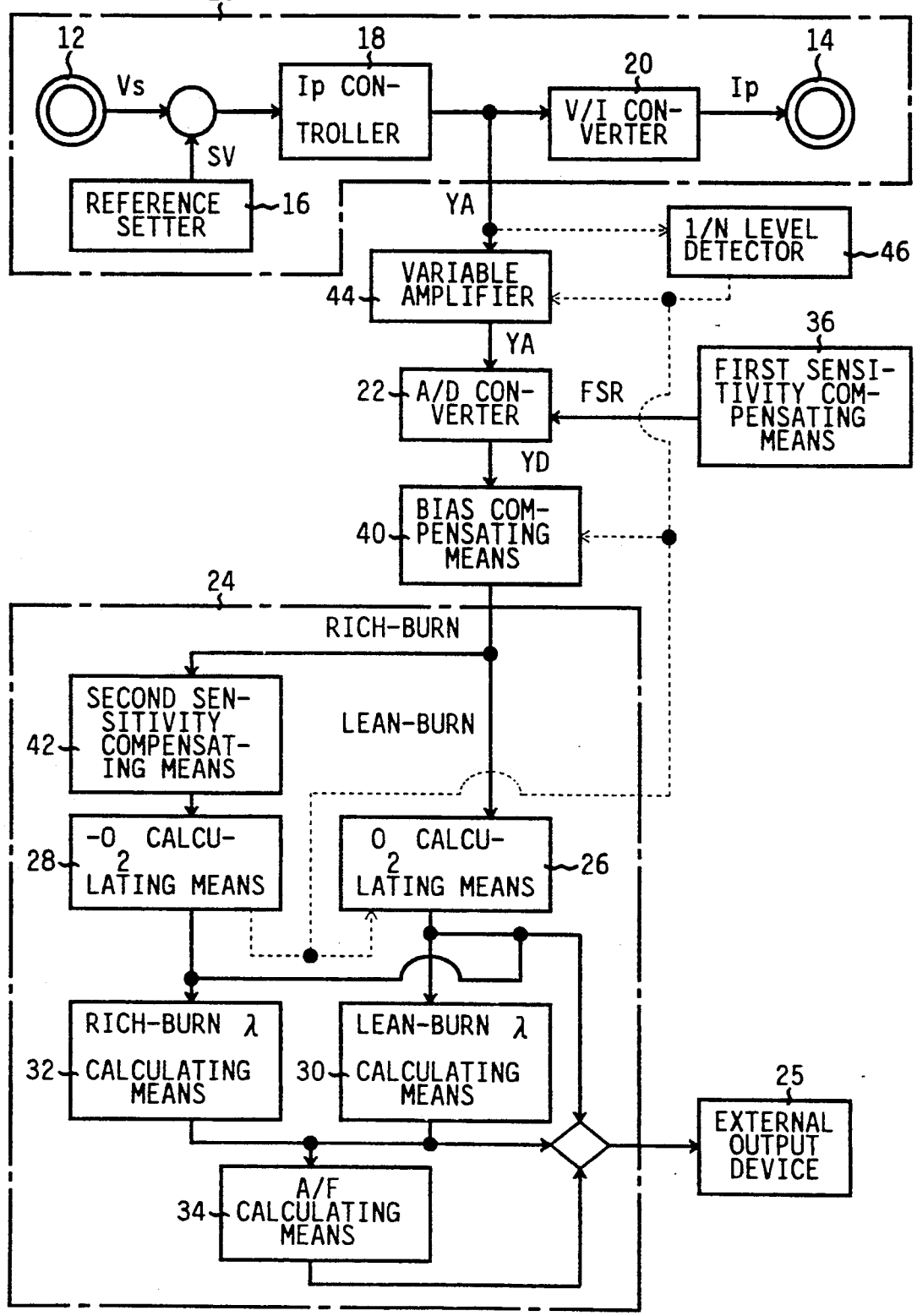
FIG. 3 is a schematic block diagram showing an output compensating method according to a second embodiment of this invention.

The first embodiment of FIGS. 1 and 2 uses the first sensitivity compensating means 36, bias compensating means 40 and second sensitivity compensating means 42, while the second embodiment of FIG. 3 uses another compensating means in the form of the selective amplifier 44 in addition to the three compensating means 36, 40, 42. However, the principle of the present invention does not require the use of three or all of these four compensating means 36, 40, 42, 44 in combination, but permits the use of any one of these compensating means, for example, the first sensitivity compensating means 36 alone.

In the illustrated embodiments, the first sensitivity compensating coefficient KA which corresponds to the current sensitivity coefficient $KO_2$ associated with the $O_2$ concentration of the exhaust gas, and the second sensitivity compensating coefficient KM which corresponds to the current sensitivity coefficients $KH_2$, $KCO_2$ associated with the $H_2$ and $CO_2$ concentrations of the exhaust gas are determined as explained above, based on the outputs of the signal processing device 24 which are actually detected when the sensor 10 is exposed to the calibrating gas whose $O_2$ concentration or $H_2$ and $CO_2$ concentrations is/are known. However, these sensitivity compensating coefficients KA and KM may be determined based on the $O_2$, $H_2$ and $CO_2$ concentration current sensitivity coefficients $KO_2$, $KH_2$ and $KCO_2$ of each specific sensor 10 which are actually measured before the sensor 10 is incorporated in the sensing system. The determined coefficients KA and KM are entered into the sensing system so that these coefficients are used by the first and second sensitivity compensating means 36, 42.

While the illustrated embodiments of FIGS. 1-3 are adapted such that the digital signal YD produced from the A/D converter 22 is subjected to the bias compensation by the bias compensating means 40, the bias compensation may be made with respect to the digital signal YA before the signal YA is applied to the A/D converter 22.

Figure 4:
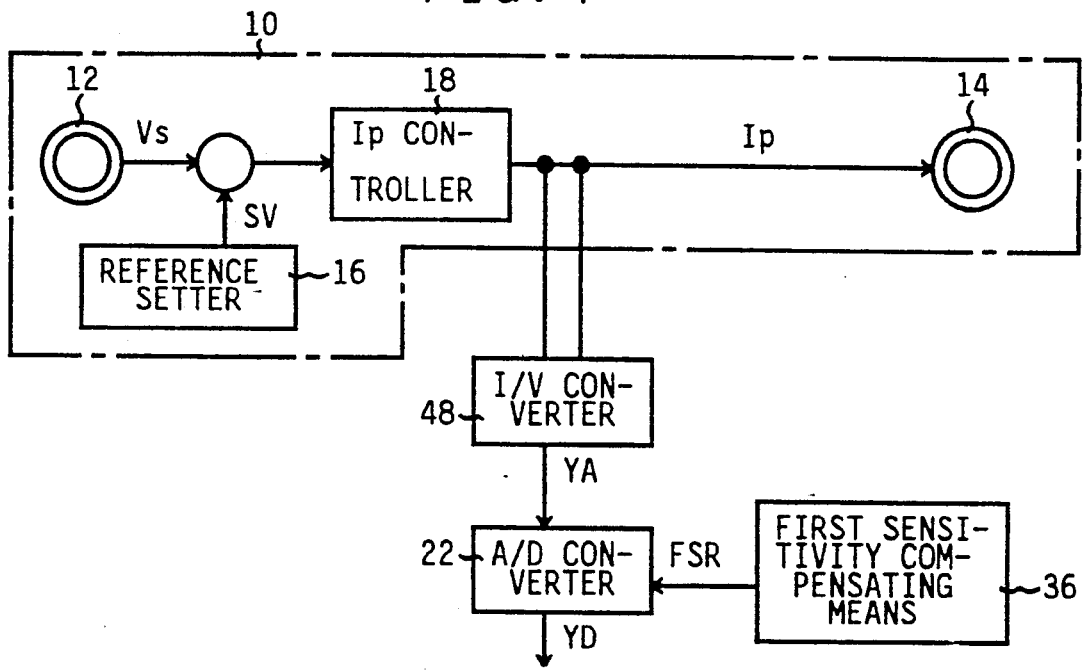
FIG. 4 is a block diagram illustrating a further embodiment of the invention wherein the output of the air/fuel sensor is a current signal, rather than a voltage signal as in the embodiments of FIGS. 1-3.

In the illustrated embodiments of FIGS. 1-3, the sensor 10 produces an analog output signal in the form of the voltage signal YA which is the output of the Ip controller 18. Where the Ip controller 18 controls the pumping cell 14 by directly applying a current signal Ip to the cell 14, this current signal Ip may be used as the output signal of the sensor 10. In this case, the current signal Ip is applied to a current/voltage converter (I/V converter) 48, as shown in FIG. 4. The I/V converter 48 converts the received current signal Ip into a voltage signal YA, which is then applied to the A/D converter 22. The voltage signal YD is processed in the same manner as in the embodiments of FIGS. 1-3.

In the embodiment of FIG. 3, the selective amplifier 44 has two positions, namely, a first position in which the received signal YA is not amplified (amplification factor=1), and a second position in which the received signal YA is amplified with the amplification factor G=N. These two positions are selected depending upon the output signal of the 1/N level detector 46. However, the selective amplifier 44 may be replaced by a variable amplifier whose amplification factor is variable in three or more steps, depending upon the level of the input signal YA.

The sensing system including the sensor 10 as described above may be used for detecting the air/fuel ratio or other parameters of an air-fuel mixture for a vehicle engine, which mixture includes alcohol. In this case, the hydrogen/carbon ratio of the fuel changes with the ratios H/C and O/C of the gasoline and alcohol and the gasoline/alcohol ratio of the fuel, and therefore the $-O_2$ calculating means 28 is preferably adapted to operate depending upon the hydrogen/carbon ratio of the fuel which is detected by suitable means for detecting the alcohol concentration of the fuel.

It will be understood that the method of compensating a sensor output can be widely used for measuring or determining the air/fuel ratio of an air-fuel mixture to be supplied to internal combustion engines of motor vehicles and various industrial furnaces.

What is claimed is:

1. A method of compensating an output signal (YA) of an air/fuel ratio sensor exposed to an exhaust gas produced as a result of combustion of an air-fuel mixture, said sensor having an internal space into which said exhaust gas is introduced under a predetermined diffusion resistance, and including a first and a second electrochemical cell each of which has an oxygen-ion conductive solid electrolyte body and at least one pair of electrodes, said first electrochemical cell operating as an oxygen concentration cell so as to produce an electromotive force (Vs) which corresponds to an oxygen partial pressure in said internal space, said second electrochemical cell performing an oxygen pumping action with a pump current (Ip) applied thereto so as to control said oxygen partial pressure in said internal space such that said electromotive force is substantially held at a predetermined constant value, said output signal corresponding to said pump current and representing a parameter of said air-fuel mixture, said method comprising the steps of:

converting said output signal in the form of an analog signal (YA) into a digital signal (YD) by an analog/digital converter;

subjecting said analog signal to a first sensitivity compensation to thereby compensate said digital signal, by adjusting an input signal range (FSR) of said analog/digital converter according to a first sensitivity compensating coefficient (KA) which corresponds to a coefficient ($KO_2$) of sensitivity of said pump current (Ip) of said sensor to an $O_2$ concentration of said exhaust gas.

2. A method according to claim 1, further comprising the steps of subjecting said digital signal compensated by said first sensitivity compensating coefficient (KA), to a bias compensation by an amount (Y0) equal to a difference between an actual output and a theoretical output of said sensor when said sensor air-fuel mixture has a stoichiometric air/fuel ratio.

3. A method according to claim 1, further comprising the step of subjecting said digital signal (YD) to a second sensitivity compensation by a second sensitivity compensating coefficient (KM) which corresponds to coefficients ($KH_2$, $KCO_2$) of sensitivity of said pump current (Ip) of said sensor to $H_2$ and $CO_2$ concentrations of said exhaust gas, if said digital signal indicates that an air/fuel ratio of said air-fuel mixture is smaller than a stoichiometric point.

4. A method according to claim 3, wherein said step of subjecting said digital signal (YD) to a second sensitivity compensation comprises:

introducing into said internal space of said sensor a calibrating gas whose $H_2$ and $CO_2$ concentrations are known;

detecting an actual level of said digital signal (YD) while said sensor is exposed to said calibrating gas; and determining said second sensitivity compensating coefficient (KM) based on a ratio of said actual level to a theoretical level which is calculated based on said $H_2$ and $CO_2$ concentrations of said calibrating gas.

5. A method according to claim 3, wherein said digital signal (YD) is subjected to said second sensitivity compensation after said digital signal is subjected to bias compensation.

6. A method according to claim 1, further comprising the steps of detecting a level of said output signal, and amplifying said output signal with an amplification factor which is determined by the detected level of said output signal.

7. A method according to claim 6, wherein said step of detecting a level of said output signal comprises determining whether or not the level of said output signal is smaller than a predetermined lower limit, and said step of amplifying said output signal comprises amplifying said output signal with a first amplification factor of 1 if the level of said output signal is not smaller than said predetermined lower limit, and amplifying said output signal with a second amplification factor larger than 1 if the level of said output signal is smaller than said predetermined lower limit.

8. A method according to claim 7, wherein said predetermined lower limit is 1/N of a nominal level of said output signal, and said second amplification factor is equal to N.

9. A method according to claim 6, wherein said analog signal (YA) is amplified with said amplification factor before said analog signal is applied to said analog/digital converter.

10. A method according to claim 1, wherein said sensor is electrically connected through said analog/digital to a signal processing device which processes said digital signal subjected to at least to said first sensitivity compensation and which includes means for calculating as said parameter an air/fuel ratio (A/F) of said air-fuel mixture.

11. A method according to claim 10, wherein said signal processing device further includes means for calculating as said parameter an oxygen excess ratio ($\lambda$) of said air-fuel mixture.

12. A method according to claim 10, wherein said signal processing device further includes means for calculating an oxygen concentration ($O_2$, $-O_2$) of said exhaust gas.

* * * * *